United States Patent [19]

Abrahams

[11] 4,070,285
[45] Jan. 24, 1978

[54] CHROMATOGRAPHY TUBE
[75] Inventor: Louis Abrahams, Worcester, Mass.
[73] Assignee: Waters Associates, Inc., Milford, Mass.
[21] Appl. No.: 644,178
[22] Filed: Dec. 24, 1975
[51] Int. Cl.² ............................................. B01D 15/08
[52] U.S. Cl. ................................ 210/31 C; 210/198 C
[58] Field of Search ............ 210/31 C, 198 C; 55/67, 55/197, 386

[56] References Cited
U.S. PATENT DOCUMENTS 3,808,125  4/1974  Good ............................... 55/386 X
3,810,545  5/1974  Filz et al. ......................... 210/198 C
3,866,308  2/1975  Halasz et al. ..................... 55/386 X Primary Examiner—John Adee
Attorney, Agent, or Firm—Irons & Sears

[57] ABSTRACT

A column for use in liquid chromatographic processes wherein the column is formed with an external reinforcing sleeve that has been found to contribute dimensional stability which results in surprising and important advantages in improving chromatographic performance. Another aspect of the invention comprises the preparation of the internal wall of the column which has an advantageous finish of 32 micro inches or better.

7 Claims, 1 Drawing Figure

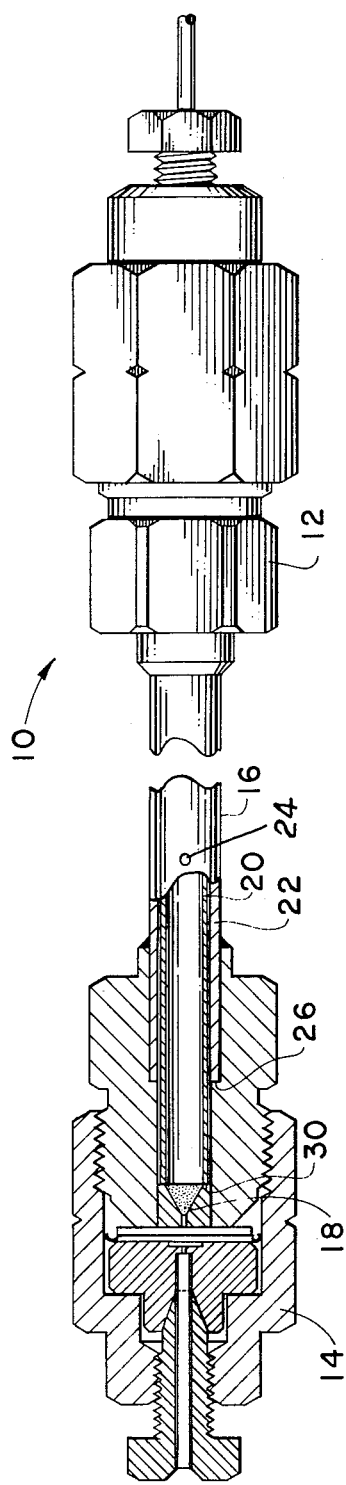

CHROMATOGRAPHY TUBE

BACKGROUND OF THE INVENTION

Liquid chromatography is a well-known procedure used in analytical and preparative chemistry. It is most commonly carried out in an elongated cylinder, usually formed of stainless steel, in which a porous chromatographic packing is immobilized. The sample to be analyzed is fed into the column in a liquid carrier. As the sample passes through the column, various components thereof are delayed for differing times because of differing interaction (chemical or physical) with the packing material. The effluent is continuously monitored to identify components as they emerge from the column.

The reproducibility of the process depends in large part on the column packing remaining in a constant condition. In the past, the primary emphasis on achieving the most dependable packing beds has been on the use of improved processes for putting the packing in place.

Many techniques have been suggested including vibration (See U.S. Pat. No. 3,300,849): All of these techniques require careful control if segregation of particles by size is to be avoided and uniformly packed columns are to be obtained. In general, the most commonly used practice of filling a high-performance column has been a costly method including slurrying the packing and passing the slurry into the column; thereby, in effect, using the column itself as a form for placing a "filter cake" of chromatographic packing therein.

A number of solutions have been suggested for holding the packing "in-place". Some of these, like the aforementioned vibration technique and slurrying technique, emphasize a maximum effort to put a conventional packing into the column in such a way as to have it assume a stable position. Other techniques, such as those described in U.S. Pat. No. 3,808,125 to Good, are rather complex or expensive procedures for fastening the packing to the column wall.

None of these attempts by the prior art have been dependably successful in achieving any of an excellent performance, a column-to-column consistency in separating characteristics, or a desired degree of stability of performance over a period of time for a single column at a cost which can make the apparatus available to the broadest spectrum of chromatographers.

In discussing packed-column processes, it is helpful to recognize four kinds of space, all of which can be referred to as "void volume." These include (1) void volume inside a porous particle; (2) theoretical void volume between particles, i.e. the type of unavoidable volume which would result from a perfectly efficient packing of spheres of the same size; (3) void volume which is attributable to imperfect packing of particles, usually present to some extent in any actual system utilizing a particulate-packing system; and (4) void volume which represents relatively large voids resulting from the consolidation of those voids described in (3). Void volume as generally used herein relates to a composite of void volumes (3) and (4).

It should be realized that the description of the prior art which is set forth above is, necessarily, made in hindsight and in view of knowledge contributed only by the instant invention. Nothing in the description is intended to be construed as an indication that the state of the prior art as described above was, or could have been, appreciated by those of ordinary skill in the art before their knowledge of the invention described below.

SUMMARY OF THE INVENTION

It is a principle object of the invention to provide an improved chromatographic column.

It is a more particular object of the application to provide a dimensionally-stable chromatographic column that will be resistant to the development of packing voids which interfere with reproducable chromatographic performance of the column.

It is a further object of the invention to provide an improved process for making a chromatographic column.

It is another object of the invention to provide an improved process for operating a chromatographic column.

It is a further object of the invention to provide a more economic and durable chromatographic column.

Another object of the invention is to provide improved processes for filling and operating chromatographic columns.

Other objects of the invention will be obvious to those skilled in the art on reading the disclosure contained herein.

The foregoing objects have been substantially achieved as a consequence of the discovery of the extreme importance of column diameter stability during repeated chromatographic use and the construction of a novel column capable of achieving such stability and the consequent extraordinary and unexpected advantage in liquid chromatography processes.

In general, the invention can be applied to liquid chromatographic columns, notwithstanding their size. However, the primary advantages of the invention are achieved when utilizing small cylinders such as those having internal diameters of less than about 0.625 inches.

The discovery that such mechanical rigidity can contribute to the performance of a chromatographic column is remarkable even in hindsight. The thermal effects on the dimensions of a column operated at several thousand psi internal pressure can be shown to far exceed the mechanical effects thereon. For example, a column operated at 5000 psi may have a 135° C outlet temperature. Yet the results of the several relatively large thermal strains on a column apparently tend to balance themselves in most cases, and the neutralization of the mechanical strain is found to be extremely advantageous.

In general, it has been found desirable to construct a chromatographic column from an elongate chamber the diameter of which will be increased by less than 0.01% when subjected to an internal pressure of 5000 psi. It is to be emphasized that the advantages of such a dimensionally stable column are not limited to chromatographic processes operated at high pressures. Substantial advantages are achieved well below 1000 psi. Moreover, it should be realized that the packing of such a column, using the slurry-packing technique wherein a filter-cake of packing is formed in the tube at high pressure, is of value in itself and allows the making of more dependable tubes.

The requisite mechanical strength of the column can be achieved by any of a number of procedures for designing strain-resistant structures commonly known to mechanical engineers and others involved in design of cylindrical pressure vessels. For example, one may balance inherent physical properties of a metal against the diameter of the column wall. Such relatively simple choices will be entirely adequate if one knows the particular applications in which a given column is to be used. In such a case, one can select a cylinder of appropriate strain-resistance based on the intrinsic properties of the metal and the thickness of the cylinder wall. This approach may be most appropriate in preparative work or in columns of such large diameter that the nature of the surface of the cylinder wall is not critical.

However, in many cases, it will be necessary to form the wetted surfaces of the column (e.g. the interior wall of the column) of a highly chemical-resistant material. Moreover, in smaller columns, i.e. those of between about 0.1 and about 0.625 inches in diameter, especially those of less than about 0.4 inches in diameter, there is believed to be a very substantial advantage to having a smooth interior column wall. The exact reason for the advantage of the finish is not known, but it is believed to facilitate an optimum packing of the column and, for that reason, to contribute markedly to column performance. Therefore, a particularly important aspect of the invention is to provide a dimensionally-stable chromatographic column which also has an improved interior surface.

It is possible to achieve a construction according to the broadest objects of the invention without use of a compound tube structure. For example, it would be possible to hard draw a tube of stainless steel (Type 316) and mechanically polish the internal surface thereof to the desired smoothness. It would be necessary to select a wall thickness for the tubing that would conform to the desired maximum diameter increase at the selected operating pressure.

ILLUSTRATIVE EMBODIMENT OF THE DISCLOSURE

In this application and accompanying drawings there is shown and described a preferred embodiment of the invention and suggested various alternatives and modifications thereof, but it is to be understood that these are not intended to be exhaustive and that other changes and modifications can be made within the scope of the invention. These suggestions herein are selected and included for purposes of illustration in order that others skilled in the art will more fully understand the invention and the principles thereof and will be able to modify it and embody it in a variety of forms, each as may be best suited in the condition of a particular case.

The drawing is an illustration, partly in section, of a chromatographic column of the invention.

Referring to FIG. 1, it is seen that a chromatographic column 10 is formed of an inlet port fitting 12, an outlet port fitting assembly 14, and a main column portion 16. It is this main column portion in which substantially all the chromatographic packing material will be placed, albeit some of it can be in parts of the fitting assembly, i.e. in cone portion 18.

Column 16 is formed of an internal sleeve 20 of Type 316 stainless steel and an external reinforcing cylinder 22 formed of heat treated type 410 stainless steel.

The construction has been found to have a number of advantages in addition which are believed to contribute to its improved performance characteristics.

The inner tube 20 has been formed by drawing it over a mandrel by a method known in the mechanical arts. This procedure allows a thin tube of excellent finish, e.g. less than 32 microinch (RMS) to be economically attained. A typical tube will have an outside diameter of 0.1755 inch and an inside diameter of 0.1535 inches (3.9 mm). The wall thickness is 0.011 inches. The inner tube is advantageously formed of a 316 stainless steel, a material selected primarily for its chemical resistance to a wide variety of chemicals. In fact, these tubes advantageously have interior finishes below 16 microinches and as low as 8 microinches.

The outer reinforcing sleeve 22 will have a wall thickness of about 0.045 inches. The inner diameter will be about 0.176 inch. The sleeve 22 is formed of a stronger material such as Type 410 stainless steel. This material has yield strength (0.2% offset) of about 150,000 psi after it is hardened; i.e. heat-treated to a Rockwell C hardness value of about 40. This compares with a yield strength of about 30,000 or 40,000 for annealed stainless steels of the 316 or 410 Types. In General, it is advantageous that the exterior tube have a (0.2% offset) yield strength of at least 90,000 psi, preferably 150,000 psig.

A very small hole 24, say 0.5 mm in diameter is drilled in the wall of the inner tube about midway between its ends.

In assemblying a column according to the invention, the tubes are cleaned well and the inner tube is inserted into the outer tube and the end fittings are positioned. At this point, the inner tube extends well beyond each end of the outer tube. The inner tube is passivated as known in the art. Next, the end fittings are brazed in place and the two tubes are brazed together, as at 26, with a compatible ferrous nickel-chrome brazing alloy. Such alloys are commonly used in brazing Type 316 stainless steel. One such alloy is sold under the trade designation Nicro 30 by Wall Colmoloy Co.

The inner tube is then pressurized internally to push it into snug contact with the outer tube. The expansion on pressurization should reach the elastic limit of the internal tube (about 12,000 psi in the specific embodiment) so that it does not return to its original dimensions, but remains in snug permanent position against the outer tube. The outer tube will also be expanded but not beyond its elastic limit. This temporary expansion of the outer tube assures the inner tube sufficient strain to exceed its elastic limit. The small hole described above serves the purpose of allowing gas to escape the space between the tubes on expansion.

The tube is cut to terminate, as at point 30. This cutting is done with a non-metallic tool, i.e. a ceramic or diamond tool, to assure that free metal will not contaminate the passivated tube surface.

It is believed that provision of a column with a superior interior surface is desirable to facilitate packing of the chromatographic packing. Thus, the preparation of the interior tube as described above is thought to be an advantageous aspect of the invention. However, the provision of an exterior reinforcing tube as taught having (1) a high resistance to creep and (2) the ability to contain very high pressures below its elastic limit is believed to result in a dimensional stability of the packed column which (1) avoids loosening the packing to the extent it can move about and allow formation of voids of the size and character which interfere with chromatographic performance and (2) assures that the tube returns to the same dimension on each removal of pressure therefrom.

Enormous improvements in quality and reproducibility of chromatographic separations have been achieved using the column and process of the invention. For example, using aqueous gel-permeation-chromatography micro-grade packings of the bonded phase ($C_{18}$) type, at columns pressures of 5500 psig, it was found that columns could be put in series with predictable and reproducible results cycled through a large number of separations. When non-reinforced prior-art columns were used for the same process (and, of course, with the same packing) troublesome voids invariably appeared in the system after a single run. Even this single run yielded inferior analytical results because of formation of voids during the run.

In general, there are advantages to using the radially-constrained column of the invention in filling of chromatographic tubes at pressures above about 2,000 psig.

It is to be understood that the following claims are intended to cover all of the generic and specific features of the invention herein described and all statements of the scope of the invention which might be said to fall therebetween.

What is claimed is:

1. In a chromatographic column of the type comprising an elongate chamber filled with a porous mass of chromatographic packing material, the improvement wherein said chamber is formed of a cylinder having a mechanical strength such that the diameter of said cylinder will be increased by less than about 0.01% when subjected to an internal pressure of 5000 psi, wherein said column comprises a relatively thin tubular sleeve of a chemically-resistant material within an exterior reinforcing tube formed of a material having relatively greater resistance to strain and wherein said exterior reinforcing tube is formed of a metal having a yield strength (0.2% offset) of over 100,000 psi and wherein said tubular sleeve is formed of stainless steel which has been expanded to the elastic limit.

2. A column as defined in claim 1 wherein said tubular sleeve has a finish of less than about 32 microinches rms.

3. A column as defined in claim 1 wherein said tubular sleeve has a finish of up to about 16 microinches rms.

4. In a column as defined in claim 1 wherein said yield strength is about 150,000.

5. In a column as defined in claim 1 wherein said chamber has a maximum diameter of 0.625 inches.

6. In a column as defined in claim 4 wherein said tubular sleeve has a finish of less than about 16 microinches rms and said chamber has a maximum diameter of 0.625 inches.

7. In the process of filling a chamber of a chromatographic column by the deposition of a filter cake of chromatographic packing therein by the passage of a slurry of packing in a liquid carrier into one end of said chamber, at a pressure of about 2,000 psig or higher, and the removal of said liquid carrier from the other end of said chamber the improvement wherein the volume of the chamber is maintained within a tolerance of 0.01% during the addition of said slurry; and wherein said tolerance is achieved by utilizing a column formed of a metal having a yield strength (0.2 offset) of over 90,000 psi and lining the interior of said column with a stainless steel tubing expanded beyond the elastic limit of said stainless steel tubing.

* * * * *